Figure 1:
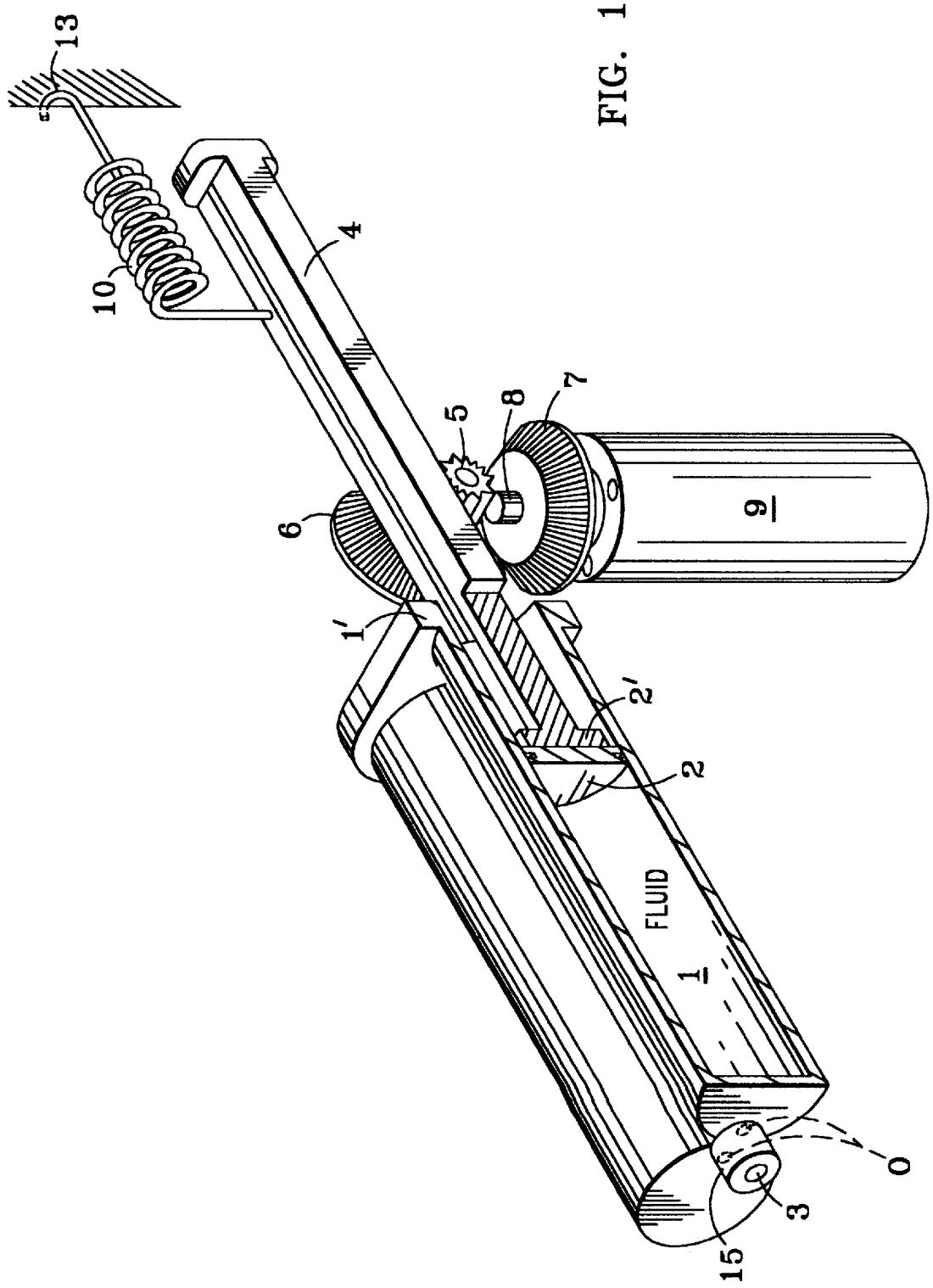

United States Patent [19]
Gardos

[11] Patent Number: 6,089,407
[45] Date of Patent: Jul. 18, 2000

[54] ELECTRICALLY POWERED FLUID-DISPERSING APPARATUS AND A METHOD PARTICULARLY ADAPTED FOR HAND GUN OPERATION

[75] Inventor: Ivan Gardos, Shrewsbury, Mass.

[73] Assignee: Dispensing Technologies International Inc.

[21] Appl. No.: 09/224,737

[22] Filed: Dec. 31, 1998

[51] Int. Cl.[7] .................................................. B67D 5/60
[52] U.S. Cl. .......................... 222/137; 222/1; 222/145.5; 222/327; 222/333
[58] Field of Search ................................ 222/137, 145.5, 222/145.6, 326, 327, 333, 386

[56] References Cited

U.S. PATENT DOCUMENTS

| | | | |
|---|---|---|---|
| 4,583,934 | 4/1986 | Hata et al. ................................ | 222/333 |
| 5,341,958 | 8/1994 | Bayat et al. ............................. | 222/333 |
| 5,450,988 | 9/1995 | Jerdee ..................................... | 222/333 |
| 5,762,239 | 6/1998 | Cossette .................................. | 222/333 |
| 5,875,928 | 3/1999 | Muller et al. .......................... | 222/145.6 |

FOREIGN PATENT DOCUMENTS

| | | | |
|---|---|---|---|
| 0343003 | 11/1989 | European Pat. Off. ............... | 222/333 |
| 6100054 | 4/1994 | Japan ..................................... | 222/137 |

Primary Examiner—Joseph A. Kaufman
Attorney, Agent, or Firm—Rines and Rines

[57] ABSTRACT

Novel hand-held single or two-component viscous fluid material dispensing gun, particularly though not exclusively useful for dental use and the like, and using in-line longitudinal drive racks and fluid cartridge containers, the racks being driven longitudinally along a barrel by an electric motor that is preferably mounted and controlled in the handle transversely depending below the barrel.

23 Claims, 3 Drawing Sheets

ELECTRICALLY POWERED FLUID-DISPERSING APPARATUS AND A METHOD PARTICULARLY ADAPTED FOR HAND GUN OPERATION

The present invention relates to the dispensing of fluids from cartridges or containers or the like; being more particularly concerned with the dispensing of multiple fluids such as two-component materials of low-to-high viscosity (resins, epoxies, adhesives, silicones, etc.) and to the instant release or commencement, and sharp termination of such fluid dispensing under operator control, including, preferably, by small compact apparatus such as electrically-powered hand gun apparatus, as for dental fluid material applications and also for more general fluid-dispensing use, as well.

BACKGROUND OF INVENTION

The art is replete with various types and sizes of pneumatic and other powered, positive displacement fluid-dispensing apparatus for a wide variety of industrial, specialized, and home applications, including, for example, viscous fluid cartridge dispensers of the type disclosed in the earlier U.S. Pat. No. 5,816,455 of the present inventor herein and of common assignee.

Where hand-held application guns are desirable, moreover, it is tedious and tiring to operate successive manually or pneumatic-triggered "shots" in jolts.

It has also been proposed to provide microprocessor-controlled and smoother electrically driven pumps, as described, for example, on p. 1025–6 of the Cole-Parmer Instrument Company instruments catalog of 1993–1994, for single or multiple-component fluid dispensing; and, where hand-held operation is desired, for providing electric motor driven rods for expelling fluids from cartridges or syringes, with a hand-held apparatus, as, for example, in U.S. Pat. Nos. 5,630,527 and 5,765,722.

In dispensers of the prior art using electric motor drives, however, the motor has generally been mounted in-line with the drive rod(s) or screw, that actuates plungers to dispense fluid from cartridges or syringes or the like, with the rod or screw often passing axially through the motor structure itself, as for example, in the last-named references. For hand-held operation with such electric motor-drive rod in-line structures, the hand holds the apparatus longitudinally like a pencil or soldering iron. There are important applications, however, as in use by a dentist within a patient's mouth, and in other applications, as well, where such in-line holding of the apparatus blocks the view required to apply and control the dispensed fluid by the operator, such as the dentist. Similarly, where the operator must have an unobstructed view of the dispensing within an enclosure or the like, such hand-held operation again blocks satisfactory viewing.

It is to the solution of these and other problems more particularly with hand-held fluid dispensing guns and the like, accordingly that the present invention is primarily directed.

The invention is also an improvement over pneumatic systems that require an air line. Because the invention provides for cordless operation via a battery pack, the system is portable and therefore useful in environments where running an air line or power cord is prohibitive.

OBJECTS OF THE INVENTION

It is an object of the present invention, therefore, to provide a new and improved method of and apparatus for fluid dispensing. and more particularly, though not exclusively, for hand-held operation, and with smooth and easy electric motor powering, that shall not be subject to the above and other disadvantages of prior devices, but, to the contrary, shall provide a vastly improved electrically powered user-friendly small multiple or single fluid dispenser, with instantaneously responsive dispensing and cut-off.

A further object is to provide a novel hand-held dispensing gun that is particularly useful for dental and other confined area usage, and the like, with open view for the operator to see and control the dispensing.

Another object is to lower the center-of-gravity of the gun for more facile hand use by incorporating the electric motor in the handle, transversely depending from the barrel.

Other and further objects will be explained hereinafter and are more particularly delineated in the appended claims.

SUMMARY

In summary, however, from one of its important aspects, the invention embraces an electrically powered gun for dispensing fluid materials having, in combination, a fluid-containing longitudinally extending cartridge chamber having an inlet sealed by a piston plug and an orificed outlet; a longitudinally extending and moveable rack mounted in-line with the cartridge chamber and provided with a terminal push pad surface adjacent the cartridge chamber piston plug; an electric drive motor mounted transversely of the rack with its drive shaft extending orthogonal to the rack and coupled by beveled gears and a pinion to drive the rack, longitudinally forward towards the cartridge chamber upon energizing the motor in order to engage the push pad surface with the piston plug and push the piston plug into the cartridge chamber to dispense the fluid through the cartridge chamber outlet.

Preferred and best mode designs and construction and method of operation are later described in detail.

DRAWINGS

Figure 2:
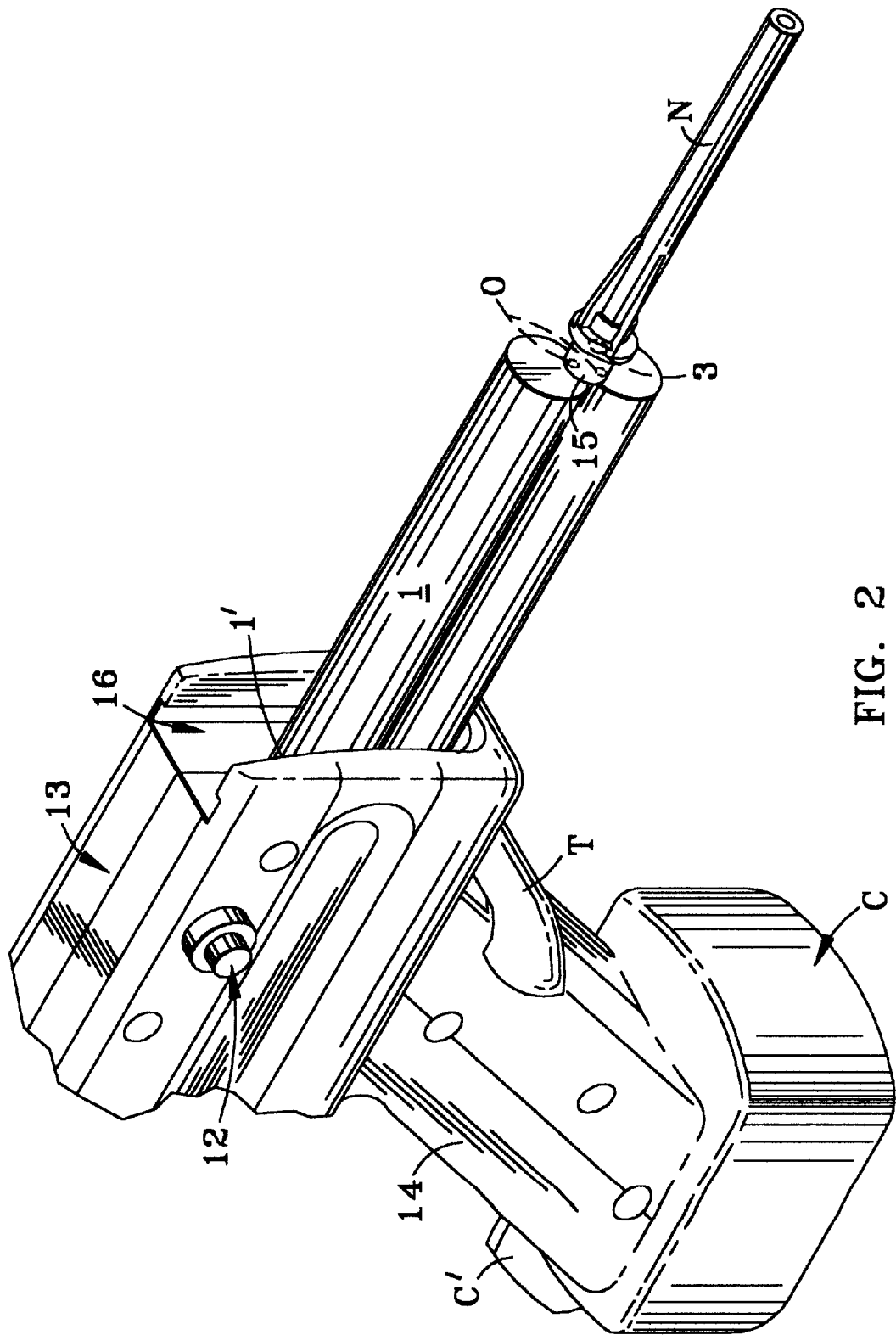
Figure 3:
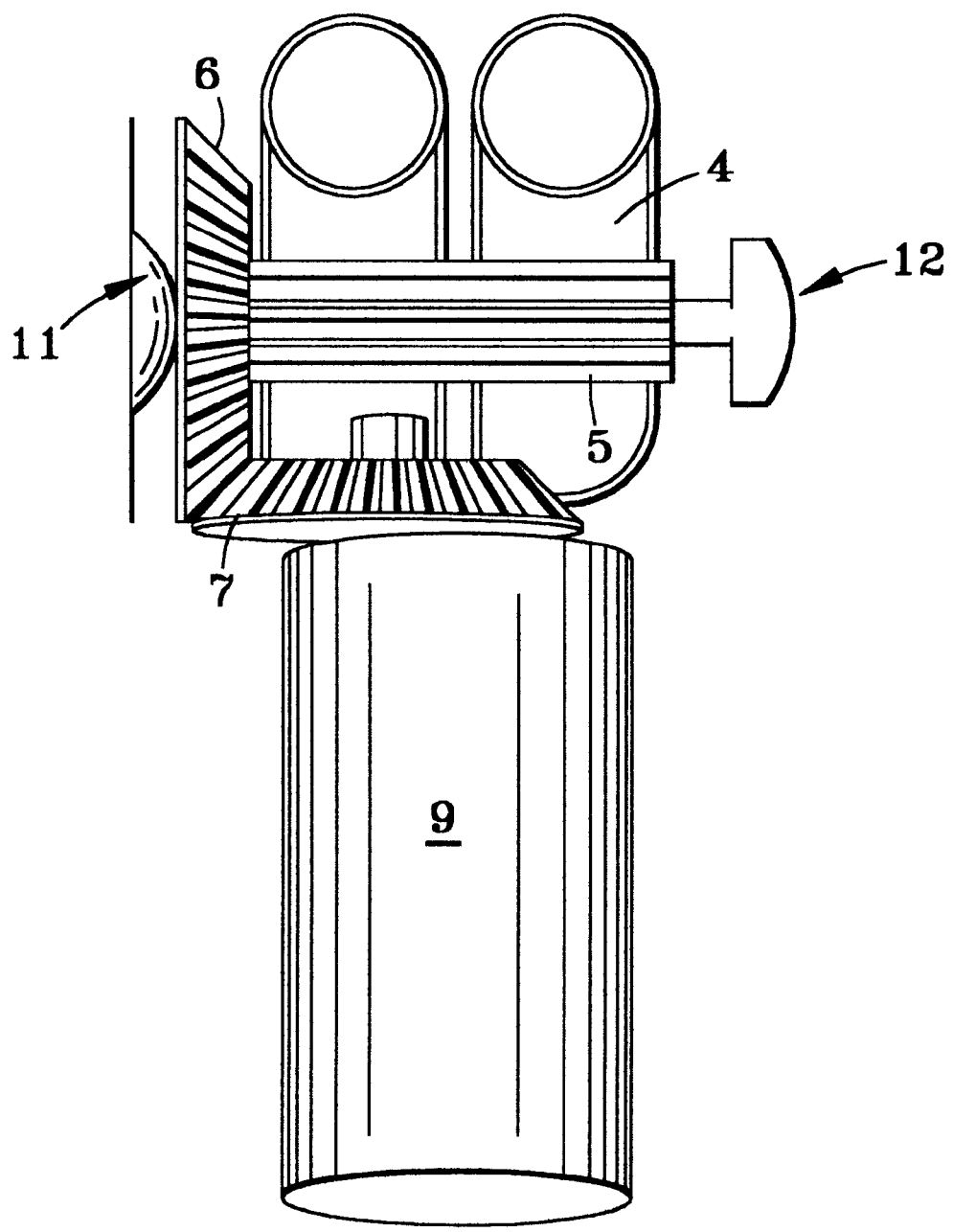

The invention will now be described in connection with the accompanying drawings, FIG. 1 of which is an isometric view, partly sectionalized, illustrating a hand gun dispenser designed in accordance with a preferred embodiment of the invention;

FIG. 2 is a similar view of the external housing containing the apparatus of FIG. 1; and FIG. 3 is a fragmentary isometric of the gear drive section of the gun of FIGS. 1 and 2, illustrating the release button mechanism.

PREFERRED EMBODIMENT(S) OF INVENTION

As shown in FIGS. 1 and 2, a longitudinally extending cartridge chamber 1 contains the material to be dispensed (as in a pair of side-by-side cartridges for multiple materials) and receives at its inlet, a piston plug or plunger 2, FIG. 1, which seals the cartridge or barrel chamber, and, when pushed longitudinally to the left in FIG. 1, forces the material in the cartridge to an orificed outlet 3 at the end (left hand, in FIG. 1, and right hand in FIG. 2). This pushing is effected in response to the operation of a longitudinally extending in-line rack and pinion type pusher assembly 4-5-6. The cartridge chamber 1 serves as the forward part of the dispensing gun barrel 13, FIG. 2, with the rack and pinion assembly occupying the rearward part of the gun barrel. The cartridge chamber is provided with an inlet collar 1' that is traversely locked into a mounting slot 16 at the front of the barrel housing 13, FIG. 2.

In preferred form, the pinion 5 is provided with a beveled gear portion 6 (shown disposed in a vertical plane), driven by another beveled gear 7 (disposed in a horizontal plane) attached to the shaft 8 of a high torque electric motor 9, FIG. 1. The shaft is an integral part of the motor and extends vertically transversely orthogonally to the barrel 1 within the handle 14 therebelow, FIG. 2. As the motor shaft turns, the bevel gear 7 turns with it and through the action of the pinion 5, turns the bevel gear 6 attached to the longitudinal pinion 5, thus driving the pusher assembly rack 4 longitudinally. This causes terminal push pad(s) 2' at the end of the rack(s), to engage against the piston plug(s) 2 for expelling material out of the orificed end 3 of the cartridge system 1. The beveled gear 6 is pressed into engagement with the beveled gear 7 by a spring washer 11, FIG. 3. During the forward pushing of the assembly 4 under the control of the high torque motor 9, a spring 10, FIG. 1, connected at one end to the pusher assembly and, at its other end, to the gun housing 13, is stretched, attempting to pull the pusher assembly back to its original position.

Once the cartridge chamber is emptied to a desired degree, the user, by pushing retract button 12, FIGS. 2 and 3, disengages gears 6 and 7, freeing the pinion assembly and enabling the tensioned or stretched spring 10 to retract or spring-return the pusher assembly back to such original starting position. The cartridge chamber 1 can then be detachably transversely removed from its mounting slot 16 in the forward part of the barrel housing 13, and is replaced by another fluid-filled cartridge chamber.

One of the novel features of the invention resides in locating the motor and its shaft and drive gear in the handle 14, depending transversely at right angles below the longitudinally extending gun barrel portion 13 that encases the pinion, rack and cartridge chamber assembly, and not in-line as in prior art devices, such as, for example, those of the earlier cited patents. This allows the user, such as a dentist or other user, in gripping and operating the handle 14, to have a clear unobstructed view of the area of dispensing, as distinguished from the blocking of the line-of-sight by the user's hand, as in prior in-line constructions. The design of the invention, moreover, through enabling a pinion system to drive the pusher rack assembly instead of straight-forward pistons, greatly facilitates disengagement from the motor to allow the rack system to snap back to its starting position, thereby speeding up the change of cartridge chambers. Such rapid change of cartridge chambers is particularly critical where fast-setting materials are dispensed. If, for example, enough material has not been dispensed when a cartridge chamber is emptied, the very rapid exchange of the empty cartridge chamber for a new fluid-filled cartridge chamber before the dispensed materials has set or hardened (in seconds), is essential. The right angle or orthogonal depending handle location for the motor, moreover, permits a lower center of gravity, making it easier for the operator to hold the handle and orient the gun, and enabling a smaller and more compact unit.

In preferred form, the rack and pinion combination with its pair of parallel rack arms and pusher pads 2', is injection molded in a single U-shaped piece. And, particularly where multiple materials are to be dispensed (resins, catalysts, etc.), there can be several versions for different ratios of material dispensing. The use of different-sized piston heads and/or different diameter cartridges, including different pre-manufactured combinations thereof, can achieve various desired ratios (1:1, 2:1, 4:1, 10:1, etc.).

In order to operate the gun, the user inserts cartridge chamber 1 into the housing 13 at the forward slot 16. The cartridge chamber aligns when it is dropped into the slot, seating the collar 1' therein. At the end 3 of the cartridge chamber, a static mixer 15 is provided, FIG. 2, for mixing the materials dispensed through small orifices O (shown dotted in FIG. 2) at the outlet end 3 of the cartridge chamber 1. In order to dispense, the user operates the trigger T in the handle 14 which then activates a switch (not shown) to turn on the motor 9. The motor then drives the mechanism as previously described to cause the cartridge material to be expelled into the static mixer 15 which mixes the compounds in the two sides of the cartridge container and ejects the mixed materials through the terminal nozzle N. At the bottom of the handle 14, furthermore, a compartment C may be provided that may contain batteries, if desired; and a connector C' is provided on the back of the battery compartment C otherwise enabling a wall mount to a transformer to bring power into the unit. The power may be varied in conventional manner, as by a speed control dial on the gun (not shown), to control the motor speed, enabling slow down when dispensing over more complex patterns, and speed up when fast performance is required.

The hand-held gun of the invention, (or optionally counter top or wall mount use and with optional battery or external powering), for the dispensing of two-component materials and the like, thus provides for easy finger trigger operation of electrically powered, motor-driven positive-displacement material dispensing, and with the release of the trigger immediately cutting off the force applied to the dispensing pistons—all as contrasted from pneumatic systems of less accuracy, having variability caused by waiting for air pressure to build up or evacuate from a pneumatic cylinder. With the rack and pinion construction of the invention, moreover, when the operator releases the trigger (switch), the unit automatically inherently retracts the push pads just slightly—causing a pressure release and fluid "suck-back" that eliminates dripping and enables sharp dispensing cut-off. The high torque electric motor of the invention, indeed, enables working with some of the highest viscosity material components, even up to 2+ million cps. This provides for operation over a wide range of choices of materials.

Further modifications will also occur to those skilled in this art, and such are considered to fall within the spirit and scope of the invention as defined in the appended claims.

What is claimed is:

1. An electrically powered gun for dispensing fluid materials having, in combination, a fluid-containing longitudinally extending cartridge chamber having an inlet sealed by a piston plug and an orificed outlet; a longitudinally extending and moveable rack mounted in-line with the cartridge chamber and provided with a terminal push pad surface adjacent the cartridge chamber piston plug; an electric drive motor mounted transversely of the rack with its drive shaft extending orthogonal to the rack and coupled by gears to drive the rack longitudinally forward towards the cartridge chamber, upon energizing of the motor, in order to engage the push pad surface with the piston plug and push the piston plug into the cartridge chamber to dispense the fluid through the cartridge chamber outlet and spring-controlled rack retracting means.

2. The dispensing gun of claim 1 wherein means is provided, operable upon de-energizing of the motor, for actuating the retracting means, withdrawing the push pad surface from the cartridge chamber.

3. The dispensing gun of claim 2 wherein the retracting means comprises a spring that becomes tensioned during the forward driving of the rack, and a return mechanism for disengaging the gears to free the rack for said retracting under spring return action.

4. The dispensing gun of claim 1 wherein the cartridge chamber comprises a pair of fluid material cartridges each having respective piston plugs, and the rack has a corresponding pair of rack arms connected to move as a unit and each having respective push pad surfaces for engaging the corresponding cartridge piston plugs to enable simultaneous dispensing of the fluid in each cartridge at their respective apertured outlets.

5. The dispensing gun of claim 4 wherein the apertured outlets of the pair of cartridges are connected with a common mixing chamber and dispensing nozzle extending therefrom.

6. The dispensing gun of claim 5 wherein the rack, gears and the electric motor are disposed within a housing having a longitudinal barrel portion internally mounting the rack and gears, and a transverse depending handle position for hand gripping of the gun and encasing the motor.

7. The dispensing gun of claim 6, wherein the cartridge chambers are detachably mountable at the forward end of the barrel portion with their respective piston plugs disposed in-line with the rack push pad surfaces.

8. The dispensing gun of claim 7 wherein the handle is provided with a finger trigger for externally controlling the energizing and de-energizing of the electric motor within the handle.

9. The dispensing gun of claim 8 wherein the housing is also provided with an external button, operable following the dispensing of the fluid from the cartridges, for actuating the disengaging of the gears to free the rack within the barrel portion for enabling its retraction.

10. The dispensing gun of claim 8 wherein the handle is provided with an internal battery compartment and with an external electrical connector for transformer powering.

11. The dispensing gun of claim 8 wherein, upon release of the trigger, the rack push pad surfaces automatically retract slightly in response to the resulting pressure release, eliminating fluid dripping at said cartridge outlets.

12. The dispensing gun of claim 7 wherein the gun is adapted for the dispensing of fluids used in dental applications and wherein, the mixing of the fluids and the dispensing thereof from the barrel through said nozzle enables the application for a desired use by a dental operator, with the used cartridge and mixing chambers and nozzle being detachably removable from the barrel for discard or reuse, and for attachment to the barrel of new fluid-filled cartridge chambers.

13. The dispensing gun of claim 6 wherein said housing is also provided with an external button, operable following the dispensing of the fluid from the cartridges, for actuating the disengaging of the gears to free the rack within said barrel position for enabling its retraction, and said spring-controlled rack retracting means comprises spring means provided within the barrel portion, connected between the rack and a point interior of the barrel, for tensioning the spring during the forward driving of the rack and for spring return action upon the operation of said button.

14. The dispensing gun of claim 13 wherein said gears comprise a beveled gear and pinion assembly.

15. The dispensing gun of claim 14 wherein the rack is a pair of parallel in-line longitudinal racks driven by the pinion.

16. The dispensing gun of claim 4 wherein the rack is formed as a one-piece U shaped member with the neck of the U positioned rearwardly, and the free ends of the arms of the U carrying the push pad surfaces.

17. An electrically powered gun for dispensing fluid materials having, in combination, a fluid-containing longitudinally extending cartridge chamber having an inlet sealed by a piston plug and an orificed outlet; a longitudinally extending and movable rack mounted in-line with the cartridge chamber and provided with a terminal push pad surface adjacent the cartridge chamber piston plug; an electric drive motor mounted transversely of the rack with its drive shaft extending orthogonal to the rack and coupled by gears to drive the rack longitudinallY forward towards the cartridge chamber, upon energizing of the motor, in order to engage the push pad surface with the piston plug and push the piston plug into the cartridge chamber to dispense the fluid through the cartridge chamber outlet, wherein means is provided, operable upon de-energizing of the motor, for rapidly retracting the rack, withdrawing the push pad surfacer from the cartridge chamber, the retracting means comprising a spring that becomes tensioned during the forward driving of the rack, and a return mechanism for disengaging the gears to free the rack for said retracting under spring return action, and wherein the cartraidge chamber comprises a pair of fluid material cartridges each having respective piston plugs, and the rack has a corresponding pair of rack arms connected to move as a unit and each having respective push pad surfaces for engaging the corresponding cartridge piston plugs to enable simultaneous dispensing of the fluid in each cartridge at their respective apertured outlets, the apertured outlets of the pair of cartridges being connected with a common mixing chamber and dispensing nozzle extending therefrom, and wherein the rack, gears and the electric motor are disposed within a housing having a longitudinal barrel portion internally mounting the rack and gears, and a transvere depending handle position for hand gripping of the gun and encasing the motor, with the cartridge chambers being detachably mountable at the forward end of the barrel position with their respective piston plugs disposed in-line with the rack push pad surfaces, the handle being provided with a finger trigger for externally controlling the energizing and de-energizing of the electric motor within the handle, and the housing being also provided with an external button, operable following the dispensing of the fluid from the cartridges, for actuating the disengaging of the gears to free the rack within the barrel portion for enabling its retraction, the handle being provided with an internal battery compartment and with an external electrical connector for transformer powering, and wherein said spring is provided within the barrel portion, connected between the rack and a point interior the barrel, for tensioning the spring during the forward driving of the rack and for said spring return action upon the operation of said button.

18. A method of hand-dispensing two-part fluids from a pair of parallel side-by-side longitudinally extending cartridges containing the fluids and having inlet and outlet ends, that comprises, attaching a pair of cartridges in-line with a longitudinally extending and moveable pair of connected parallel racks disposed within a longitudinal dispensing gun barrel; electrically powering the forward longitudinal movement of the racks from a handle region transversely therebelow under the control of an operator holding the handle; operating the racks to extend them forwardly into the cartridge inlets to dispense the fluids out of the cartridge outlets; mixing the dispensed fluids together in a chamber connected to the outlets, and ejecting the combined fluids; and, upon such dispensing, spring retracting the racks into the barrel, detaching the pair of cartridges and chamber for discard or reuse, and attaching a further pair of fluid-filled cartridges in-line with the retracted racks.

19. The method of claim 18 wherein the two-part fluids are fluids used in mixed combination as in dental and other applications, and the said control of the electrical powering is effected by the controlling of an external finger trigger by the operator during holding of the handle.

20. The method of claim 19, wherein said operator controls the retracting of the racks by operation of a retract button control externally on the housing.

21. The method of claim 19 wherein the ratio of the fluids dispensed from the pair of cartridges is controlled by varying one of the size of the respective push pad surfaces, and the relative degree of insertion into the respective cartridges.

22. The method of claim 19 wherein the dispensing speed is controlled by varying the electrical powering.

23. The method of claim 19 wherein, upon release of the trigger, the resulting pressure release causes the racks automatically to retract slightly, eliminating fluid dripping at the cartridge outlets.

* * * * *